(12) United States Patent
Oikawa

(10) Patent No.: US 8,452,066 B2
(45) Date of Patent: May 28, 2013

(54) IMAGE PROCESSING APPARATUS, IMAGE PROCESSING METHOD, AND PROGRAM

(75) Inventor: Michio Oikawa, Machida (JP)

(73) Assignee: Hitachi Medical Corporation, Tokyo (JP)

( * ) Notice: Subject to any disclaimer, the term of this patent is extended or adjusted under 35 U.S.C. 154(b) by 344 days.

(21) Appl. No.: 12/810,918

(22) PCT Filed: Dec. 25, 2008

(86) PCT No.: PCT/JP2008/073519
§ 371 (c)(1),
(2), (4) Date: Jul. 30, 2010

(87) PCT Pub. No.: WO2009/101754
PCT Pub. Date: Aug. 20, 2009

(65) Prior Publication Data
US 2011/0019890 A1 Jan. 27, 2011

(30) Foreign Application Priority Data
Feb. 13, 2008 (JP) ................ 2008-031992

(51) Int. Cl.
*G06K 9/00* (2006.01)
(52) U.S. Cl.
USPC .......... 382/131; 382/132; 382/128; 382/173; 345/424; 345/419; 345/427
(58) Field of Classification Search
USPC ............... 382/131, 132, 128, 173; 345/424, 345/419, 427
See application file for complete search history.

(56) References Cited

U.S. PATENT DOCUMENTS
2006/0050963 A1* 3/2006 Suzuki et al. ............. 382/190
2006/0262969 A1 11/2006 Matsumoto

FOREIGN PATENT DOCUMENTS
JP 2006-323653 A 11/2006

OTHER PUBLICATIONS

Matsumoto, a machine translated English version of JP2006-323653, Nov. 30, 2006.*
"Oh, I see!! Medical three-dimensional image; Bible of Way of thinking and Processing method", supervised by Yutaka Imai, p. 141 (2003).

* cited by examiner

Primary Examiner — Kathleen Y Dulaney
Assistant Examiner — Ruiping Li
(74) Attorney, Agent, or Firm — Mattingly & Malur, PC

(57) ABSTRACT

A processing is executed for identifying an image area which blocks an observation target, and removing the identified area. An image processing apparatus 10 is provided, which allows multiple projection drawings to be generated by projecting a three-dimensional image from any projecting direction and determines a removal target area, out of the designated area in each projection drawing. The image processing apparatus 10 is provided with an input section 40 for allowing a user to roughly specify an image area that blocks the observation target, the image area forming a maximum area, and an area judgment section 32 for identifying a removal target image area, and an image processing section 31 for constructing an image where the removal target image area has been removed.

7 Claims, 13 Drawing Sheets

IMAGE PROCESSING APPARATUS, IMAGE PROCESSING METHOD, AND PROGRAM

BACKGROUND

The present invention relates to a technique for detecting a specific image area and performing a removal process.

There is known a technique such as a volume rendering for generating a two-dimensional projection drawing from a three-dimensional image (volume data) which is made up of tomographic images (angio data) of a test object, the tomographic images being obtained by a tomographic apparatus such as an X-ray CT (Computed Tomography) apparatus and an MRI (Magnetic Resonance Imaging) apparatus.

The MIP (Maximum Intensity Projection) method is one of the volume rendering techniques. The MIP method is a method for applying a projection process to the volume data in an optional direction, and displaying on a projection plane, a maximum luminance value in the projection path. With this method, if there exists an area where bones and the like are displayed, which may hamper the observation of blood vessels or the like being a diagnostic object on the projection plane, a user has been allowed to select to a high degree of detail, the area which is desired to be removed. Accordingly, it has been possible to create a display where such area is removed (see, "Oh, I see!! Medical three-dimensional image; Bible of Way of thinking and Processing method", supervised by Yutaka Imai, p. 141 (2003)(non-patent document 1), for instance).

SUMMARY

However, according to the technique described in non-patent document 1, the user has been required to designate an area on the display screen in detail, i.e., only the area to be removed, in order to execute removing of the area such as bones and the like. Therefore, it has been necessary to perform complicated removal works.

Given the situation above, an object of the present invention is to provide a technique which utilizes that a luminance value is higher in a bone area than in a blood vessel area, thereby estimating the bone area from a roughly designated area, and enables execution of a process for removing a desired area from the display screen, just by a simple removal operation.

In order to solve the problem above, an image processing apparatus according to the present invention provides a technique which identifies a removal target area from an image area.

By way of example, it is directed to an image processing apparatus which projects a three-dimensional image from any projecting direction, and generates multiple projection drawings, the apparatus having an input accepting section for displaying the multiple projection drawings on a display part and accepting an input of a designated area which includes a removal target area as to each of the projection drawings, a luminance value calculation section for specifying a luminance value of the removal target area from the designated area, and an area judgment section for determining as the removal target area, an area where the luminance value belongs to a specific range, out of the image on a virtual ray that projects the designated area, with respect to each of the multiple projection drawings.

As described above, according to the present invention, it is possible to provide a technique that enables a bone area as the removal target to be estimated based on the luminance value of the designated area that the user has designated roughly on the projection drawing, whereby the user is allowed to remove a desired area by a simple removal operation.

DENOTATION OF REFERENCE NUMERALS

10•60: IMAGE PROCESSING APPARATUS, 20: STORAGE PART, 21: ANGIO DATA STORAGE AREA, 22: VOXEL DATA STORAGE AREA, 23: PIXEL DATA STORAGE AREA, 30•70: CONTROL PART, 31•71: IMAGE PROCESSING SECTION, 32•72: AREA JUDGMENT SECTION, 33: LUMINANCE VALUE RANGE CALCULATION SECTION, 73: LUMINANCE THRESHOLD CALCULATION SECTION, 40: INPUT PART, 50: DISPLAY PART, 610: VOLUME DATA, 600•620: PROJECTION DRAWING, 621: PIXEL, 700: DESIGNATED AREA, 80: BONE AREA, 90: BLOOD VESSEL, 800: REMOVAL TARGET AREA

BEST MODE FOR CARRYING OUT THE INVENTION

Hereinafter, preferred embodiments of the present invention will be explained, with reference to the accompanying drawings.

Figure 1:
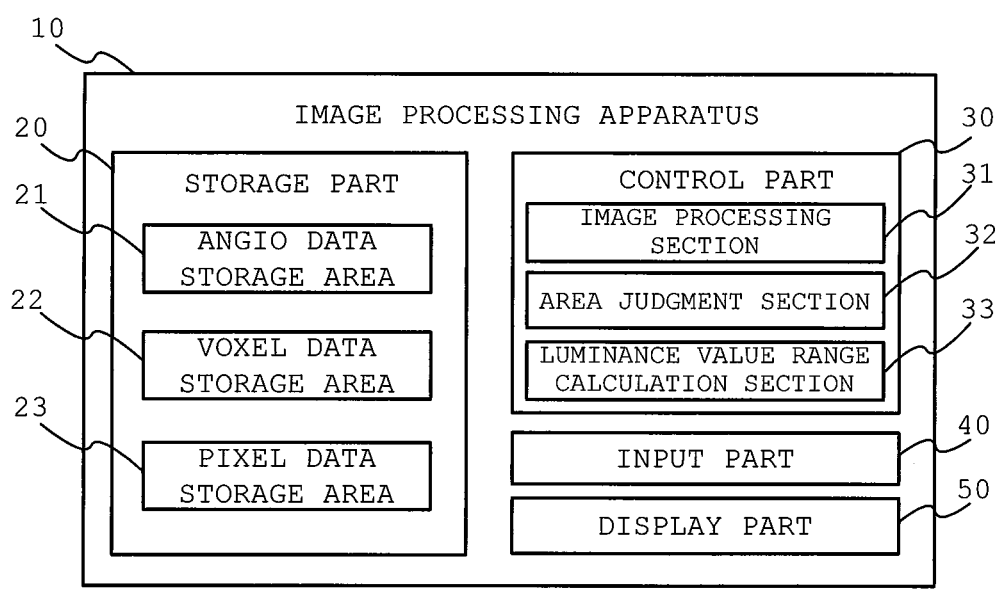
FIG. 1 is a block diagram showing a functional configuration of the image processing apparatus relating to the first embodiment of the present invention.

FIG. 1 is a block diagram showing a functional configuration of the image processing apparatus 10 relating to the first embodiment according to the present invention.

As illustrated, the image processing apparatus 10 is provided with a storage part 20, a control part 30, an input part 40, and a display part 50.

The storage part 20 incorporates an angio data storage area 21, a voxel data storage area 22, and a pixel data storage area 23.

The angio data storage area 21 stores angio data which is a three-dimensional image made up of multiple two-dimensional tomographic images which are obtained by a tomographic apparatus (not illustrated) that takes images of a specific portion respectively at positions each being spaced every predetermined distance.

Figure 2:
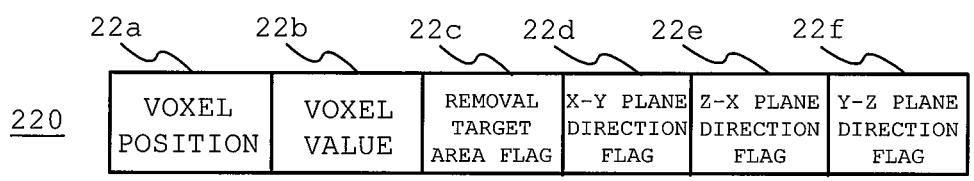
FIG. 2 is a schematic diagram showing a voxel data table.

The voxel data storage area 22 stores a voxel data table 220 in units of voxel; the table storing volume data which is made up of the angio data. As shown in FIG. 2, the voxel data table 220 includes a voxel position storage field 22a, a voxel value storage field 22b, a removal target area flag storage field 22c, an X-Y plane side direction flag storage field 22d, a Z-X plane side direction flag storage field 22e, and a Y-Z plane side direction flag storage field 22f.

The voxel position storage field 22a stores a voxel coordinate position (X, Y, Z) which is a constitutional element of the volume data. The voxel value storage field 22b stores a voxel luminance value (voxel value V) at the voxel position (X, Y, Z) which is identified by the voxel position storage field 22a. The removal target area flag storage field 22c stores a removal target area flag, which is set when the voxel identified by the voxel position (X, Y, Z) is judged as a bone area.

When the voxel at the voxel position (X, Y, Z) identified by the voxel position storage field 22a is judged as a bone area candidate, a direction flag is set in the X-Y plane side direction flag storage field 22d, in the Z-X plane side direction flag storage field 22e, and in the Y-Z plane side direction flag storage field 22f, respectively, in the following cases; the case where the projecting direction of the projection drawing including the designated area which is used as a basis for the judgment, is the X-Y plane side direction, the case where it is the Z-X plane side direction, and the case where it is the Y-Z plane side direction.

It is to be noted here that a pixel is obtained by developing a point into the two-dimensional direction (X, Y), and a voxel is obtained by developing the pixel further into the Z-direction. The voxel is a cube having information items respectively in the X, Y, and Z directions, which constitute the voxel data, and a luminance value (voxel value V) and opacity are assigned to each voxel.

Figure 3:
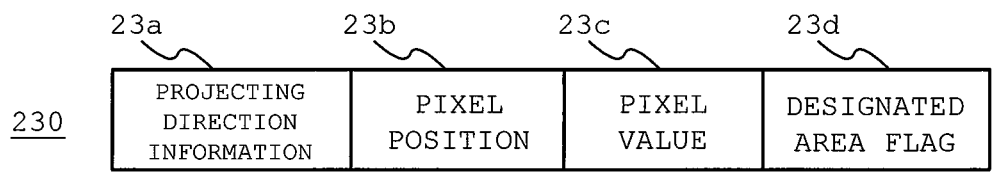
FIG. 3 is a schematic diagram showing a pixel data table.

The pixel data storage area 23 stores a pixel data table 230 for storing the projection drawing in the units of pixel, the drawing being obtained by projecting the volume data from any projecting direction. As shown in FIG. 3, the pixel data table 230 includes a projecting direction information storage field 23a, a pixel position storage field 23b, a pixel value storage field 23c, and a designated area flag storage field 23d.

The projecting direction information storage field 23a stores projecting direction information for specifying the projecting direction of the projection drawing. The projecting direction information indicates any direction in which the control part 30 projects the volume data. For example, the direction may be represented by coordinate axes based on the developing direction of the volume data, such as the direction of the X-Y plane side (front direction), the direction of the Y-Z plane side (lateral direction), and the direction of the Z-X plane side (upper direction), (see FIG. 5(a) to FIG. 5(c)), or represented by an identifier such as a numerical character.

The pixel position storage field 23b stores each of the coordinate positions (X, Y) of the pixels, each being a constitutional element of the projection drawing. Here, the pixels are generated when the volume data is projected in the projecting direction that is stored in the projecting direction information storage field 23a.

The pixel value storage field 23c stores each luminance value of the pixel (pixel value P) which is identified, by the projecting direction that is stored in the projecting direction information storage field 23a and the pixel position (X, Y) which is specified in the pixel position storage field 23b.

The designated area flag storage field 23d sets a designated area flag, when it is judged that the pixel, which is identified by the projecting direction stored in the projecting direction information storage field 23a and the pixel position (X, Y) specified in the pixel position storage field 23b, is included in the designated area, having been designated by a user.

The control part 30 is provided with an image processing section 31, an area judgment section 32, and a luminance value range calculation section 33.

The image processing section 31 executes a process to generate a projection drawing from the volume data according to the MIP method. In addition, it reconstructs the volume data based on the information stored in the voxel data table 220.

The area judgment section 32 identifies the following areas; a designated area which is designated by the user on the projection drawing, a bone candidate area within the volume data, the area being determined by the pixel value P of the pixel within the designated area, and a removal target area (bone area) in the volume data, the area being determined based on the bone candidate area.

The luminance value range calculation section 33 generates a histogram indicating a distribution with respect to each segment, as to the pixel value P of the pixel within the designated area, executes a process for specifying a cluster of the bone area, and calculates the luminance value range Cr. Hereinafter, with reference to FIG. 4 and FIGS. 5 (5(a) to 5(d)) process executed by the control part 30 will be explained specifically.

Figure 4:
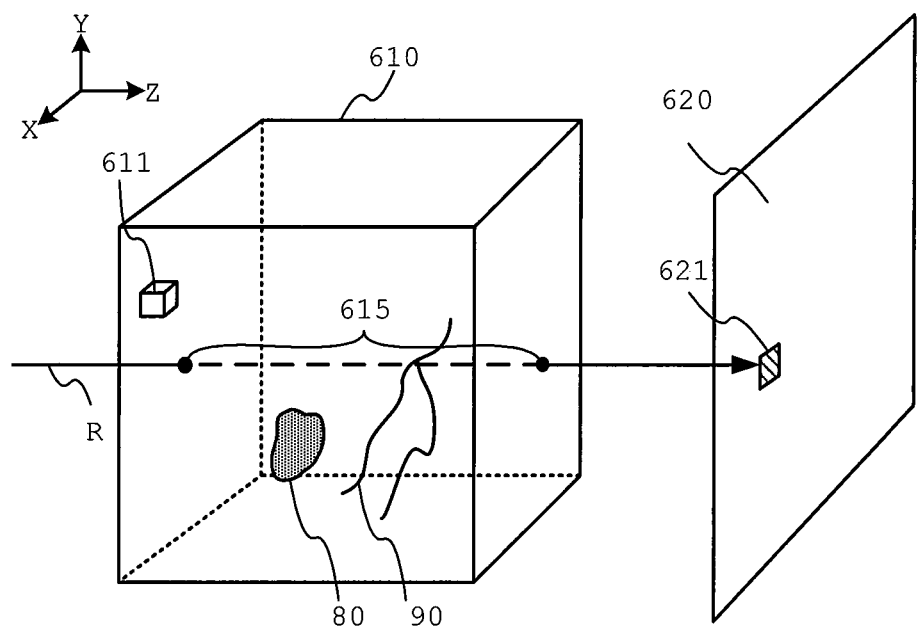
FIG. 4 is a schematic diagram showing a process for creating a projection drawing by using the volume data.

FIG. 4 is a schematic diagram showing a process for generating the projection drawing 620 by using the volume data 610. FIG. 5(a) is a schematic diagram showing a projection drawing 620a viewed from the direction of the X-Y plane (front) side of the volume data 610, FIG. 5(b) is a schematic diagram showing a projection drawing 620b viewed from the direction of the Y-Z plane (lateral) side of the volume data 610, FIG. 5(c) is a schematic diagram showing a projection drawing 620c viewed from the direction of the Z-X plane (top) side of the volume data 610; and FIG. 5(d) is a schematic diagram showing a projection drawing 600 viewed from the direction of the X-Y plane (front) side of the volume data 610 where the removal target area has been removed.

The image processing apparatus 10 relating to the present embodiment stores two-dimensional tomographic images (angio data) taken by a tomographic apparatus (not illustrated) or the like, in the angio data storage area 21 in the storage part 20. Then, the image processing section 31 reconstructs the angio data at multiple positions associated with the same phase and generates the volume data 610 which is a three-dimensional image.

As shown in FIG. 4, however, in the volume data 610, in addition to the blood vessel 90 as an observation target, an image such as the bone area 80 is taken, which blocks the observation of the blood vessel 90. Therefore, the control part 30 firstly executes a process using the MIP method so as to remove the bone area 80 assuming that this area is the removal target area 800 and display the overview image of the blood vessel 90. The MIP method is a method for converting the volume data 610 into a two-dimensional image.

The image processing section 31 irradiates the volume data 610 with a virtual ray R, as to each voxel which is a constitutional unit of the volume data, from an optional direction (in the present embodiment, it is one of three directions; the direction of the X-Y plane (front) side, the direction of the Y-Z plane (lateral) side, and the direction of the Z-X plane (top) side). Then, a maximum voxel value Vmax is detected from a group of N voxels 615, which exist on the virtual ray R. In addition, the image processing section 31 defines the detected value as a pixel value P of a pixel 621 on the projection drawing 620, the pixel 621 existing on the virtual ray R. Then, the projection drawing 620 is generated (reference symbol 620a indicates the projection drawing in the direction of the X-Y plane side, 620b indicates the projection drawing in the Y-Z plane side, and 620c indicates the projection drawing in the direction of the Z-X plane side).

The area judgment section 32 displays each of the projection drawings (e.g., FIG. 5(a) to FIG. 5(c)) on a display unit 5 which is provided in the display part 50. Then, via the input part 40, the area judgment section accepts from the user an operation for selecting a roughly designated area in such a manner that the bone area 80 forms a maximum area within the designated area on the projection drawings 620a to 620c. It is to be noted that the designated area may contain the pixels representing the blood vessel and the like. The area being designated is determined as the designated area 700 in the unit of pixels, and the area judgment section 32 specifies the pixel positions of the pixels included in the designated area 700.

The area judgment section 32 detects a voxel having the voxel value V falling into the luminance value range Cr, which will be described below, as to the voxels existing on the virtual ray R that projects the pixel within the designated area 700, and identifies the detected voxel as the bone candidate area. In addition, the voxels judged as corresponding to the bone candidate area as to all the projecting directions, are determined as the removal target area 800 which is targeted for removal.

The luminance value range calculation section 33 executes a clustering process as described below, as to the pixels within the designated area 700, and calculates the luminance value range Cr, so as to specify the luminance value of the pixel and the voxel which are determined as the bone area candidate.

It is to be noted that the angio data stored in the angio data storage area 21 may be acquired through any kind of method. For example, an interface part directly connected to the tomographic apparatus is provided to directly acquire the angio data from the tomographic apparatus. Alternatively, a communication part is provided, and the angio data may be acquired from a network such as the Internet.

The input part 40 is a user interface for accepting an input from an operator, and includes a pointing device or the like for manipulating graphics which indicate an intended operation on a GUI. The pointing device may be a mouse, or a touch panel for a direct touch on the screen, for instance.

The display part 50 is provided with a display unit for displaying at least each of the images being generated, and a CRT (Cathode Ray Tube), an LCD (Liquid Crystal Display) or the like may be selected as the display unit.

Figure 13:
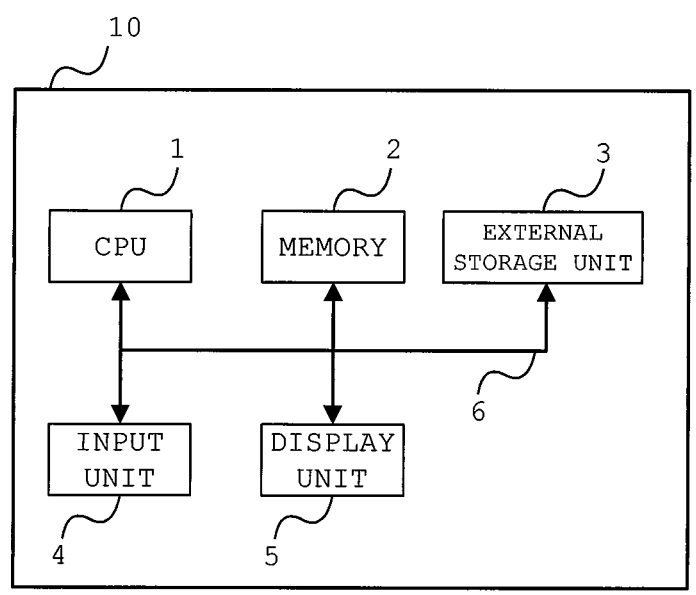
FIG. 13 is a block diagram showing an electrical configuration of the image processing apparatus relating to the first embodiment of the present invention.

Here, a hardware configuration of the image processing apparatus 10 will be explained. FIG. 13 is a block diagram indicating an electrical configuration of the image processing apparatus 10.

As shown in FIG. 13, the image processing apparatus 10 is a general computer on which programs are operated, and it may be a personal computer or a work station, for instance.

The image processing apparatus 10 incorporates a CPU (Central Processing Unit) 1 which is a major portion of the computer for collectively controlling each unit, and a memory 2 for storing various data in a rewritable manner. The image processing apparatus 10 is further provided with an external storage unit 3 for storing various programs, data generated by the programs, and the like, an input unit 4 such as a keyboard and a mouse for giving various operational instructions, and a display unit 5 for displaying image data and the like. Each of these units is connected to the CPU 1 via a signal line 6 such as a bus. It is a matter of course that the image processing apparatus is additionally provided with a communication unit for establishing communication with an external unit.

The CPU 1 loads on the memory 2, the programs stored in the external storage unit 3, and executes the programs, thereby implementing various processes. As a manner of course, the programs may also be downloaded on the external storage unit 3 from the network via the communication unit, and then they are loaded on the memory 2 to be executed by the CPU 1.

The external storage unit 3 is provided with an HDD (Hard Disk Drive) but it is not limited to the HDD, and it may be further provided with a drive of a CD-ROM, DVD-ROM or the like, as a mechanism for reading computer software being a distributed program and data.

Figure 7:
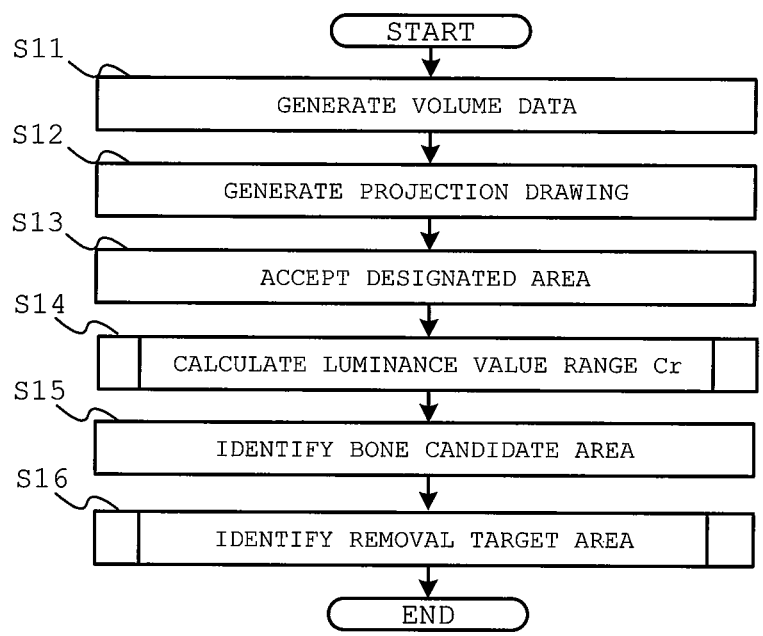
FIG. 7 is a flowchart showing a flow of the process in the image processing apparatus relating to the first embodiment.

With reference to the flowchart as shown in FIG. 7, an explanation will be made as to the process performed in the image processing apparatus 10 according to the present embodiment configured as described above.

Firstly, the image processing section 31 of the image processing apparatus 10 reads any angio data stored in the angio data storage area 21, and accumulates and reconstructs multiple images associated with the same phase on the axis, thereby generating the volume data (S11).

In addition, the image processing section 31 stores information as to each voxel being the constitutional element of the volume data, in the voxel data table 220 which is stored in the voxel data storage area 22. In other words, the image processing section stores the coordinate position (X, Y, Z) of each voxel in the voxel position storage field 22a, and stores a voxel value V specified by the voxel position storage field 22a in the voxel value storage field 22b.

Next, the image processing section 31 projects the volume data being generated, from any projecting direction according to the aforementioned MIP method, and generates multiple projection drawings (S12). In the present embodiment, it is assumed that three projection drawings are generated, which are projected from three directions, the X-Y plane side, the Y-Z plane side, and the Z-X plane side.

In addition, the image processing section 31 stores information as to each pixel being a constitutional element of these projection drawings, in the pixel data table 230 which is stored in the pixel data storage area 23. In other words, the image processing section stores the projecting direction information specifying the projecting direction of each projection drawing made up of the pixels, in the projecting direction information storage field 23a, the coordinate position (X, Y) of each pixel of the projection drawing, which is projected from the projecting direction stored in the projecting direction information storage field 23a, in the projecting direction information storage field 23b, and a pixel value P of the pixel specified by the projecting direction information storage field 23a and the pixel position storage field 23b, in the pixel value storage field 23c.

Next, the area judgment section 32 displays each of the projection drawings on the display unit 5 provided in the display part 50, and accepts as a designated area, a rough designation of bone area in which the bone area forms a maximum area (S13). By way of example, when a user specifies the designated area, the area judgment section 32 detects a projecting direction of the projection drawing as to which the designated area is specified on the display unit 5, and specifies a record which stores the projecting direction that agrees with the detected projecting direction, in the projecting direction information storage field 23a of the pixel data table 230. Then, the area judgment section further extracts a record which is stored in the pixel position storage field 23b of the record being specified, the pixel position that agrees with the coordinate position of the pixel within the designated area. Subsequently, the area judgment section 32 sets a designated area flag in the designated area flag storage field 23d of the record being extracted, and specifies the pixel corresponding to the designated area.

Any method may be employed for specifying the designated area. By way of example, it is possible to configure such that the user uses a mouse or the like to draw a free closed curve, so as to decide the designated area. In such a case, a GUI may be utilized; in the GUI, a left-click on the mouse may allow a decision of the area having a specified size, and a right-click on the mouse may allow a release of designation of the area. Alternatively, the area may be specified by changing the size or the position of a preset circle or the like.

Figure 8:
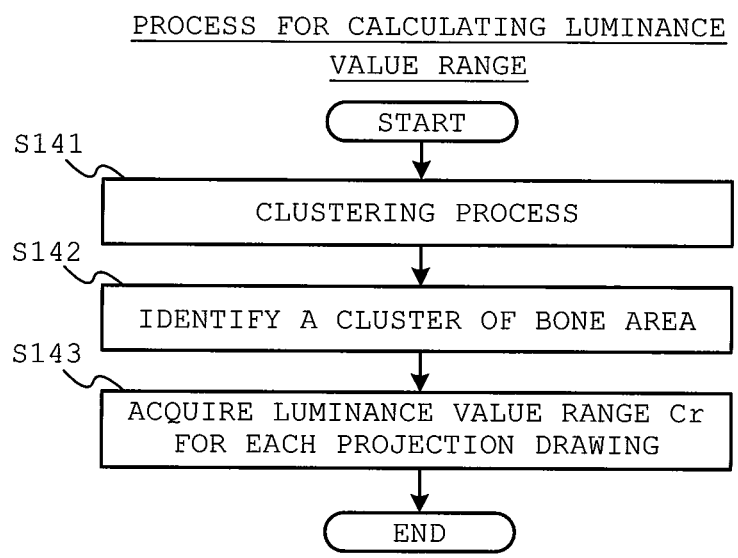
FIG. 8 is a flowchart showing a flow of a process for calculating a luminance value range in the image processing apparatus relating to the first embodiment.

Next, the luminance value range calculation section 33 calculates a luminance value range (S14). With reference to the flowchart as shown in FIG. 8, an explanation will be made regarding a process for calculating the luminance value range.

The luminance value range calculation section 33 firstly executes a clustering process as to the range of the pixel value (S141).

Figure 6:
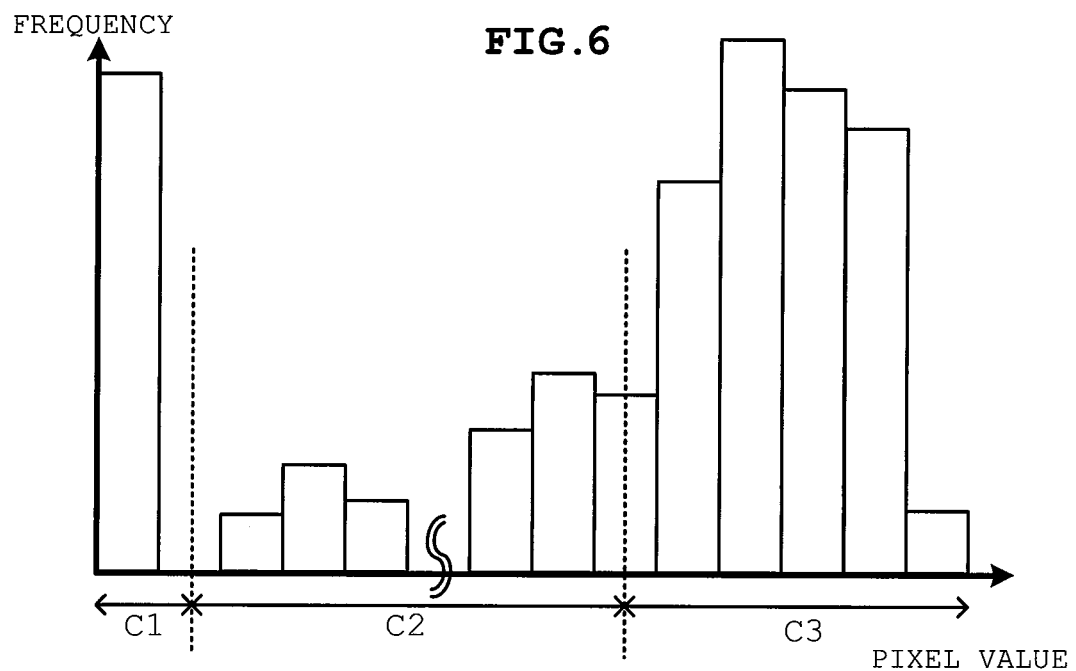
FIG. 6 is a histogram as to the pixels within the designated area.

FIG. 6 is a histogram showing a distribution of the pixels as to all the pixels included in each designated area, with the vertical axis representing a frequency (number of times), and the horizontal axis representing segments of the pixel value P. By way of example, the luminance value range calculation section 33 divides the segments of the pixel value P into clusters. In the histogram shown in FIG. 6, the range of the pixel value P is divided into three clusters C1, C2, and C3.

A publicly known method, the Fuzzy C-Means (FCM) or the like which employs a membership function, may be used as the clustering process. The FCM is a method obtained by expanding the K-Means by adding an idea of belonging degree.

The K-Means is a clustering method used in the case where the number of clusters (K) is determined in advance, and the present embodiment requires at least three clusters; the background area, the blood vessel area, and the bone area.

Firstly, an appropriate center value is given as a representative point of the cluster, and each element is made to belong to the cluster having the closest center value, and a membership value of each pixel relative to the center value (belonging degrees to all the clusters) is obtained. The pixel may belong to multiple clusters simultaneously. Subsequently, a new cluster center value is calculated based on the membership value for each of the clusters, and a new cluster is obtained. This operation is repeated until each center value stops changing, and clustering is completed at the stage reaching a designated parameter (convergence condition) or less.

The parameters (the number of clusters, the membership function, parameters (convergence condition), and the like) which are necessary for the clustering may be certain values determined in advance, or they may be values which a user is allowed to input optionally.

The luminance value range calculation section 33 further identifies a cluster representing the pixels that correspond to the bone area, out of the clusters (S142).

Here, in the present embodiment, in the designated area that the user roughly specifies by hand in such a manner that the bone area forms the maximum area, it is considered that the pixels representing the bone area form the largest range. It is further possible to assume that there mainly exist pixels representing blood vessels having a pixel value P smaller than the bone area, and a background area having a pixel value P which is much smaller than the pixels representing the blood vessels.

In the histogram shown in FIG. 6, the cluster C1, for instance, has a minimum pixel value P, and the range of the pixel value P is also small. Therefore, it is assumed that the cluster C1 is a group of pixels representing the background area. The cluster C2 has the pixel value P and the frequency, both smaller than the cluster C3, and therefore, it is assumed as a group of pixels representing the blood vessels. The cluster C3 has the pixel value P and the frequency, both being large, and it is assumed as a group of pixels representing the bone area forming a large area within the designated area.

Therefore, in the present embodiment, the luminance value range calculation section 33 identifies the cluster C3 as the bone area pixels. A method for identifying the bone area and the clustering process are not limited to those described above, and any method may be applicable.

Subsequently, the luminance value range calculation section 33 calculates the luminance value ranges Cr1, Cr2, and Cr3 respectively for the designated areas of the projection drawings (Cr1: luminance value range of the designated area in the projection drawing in the X-Y plane side direction, Cr2: luminance value range of the designated area in the projection drawing in the Z-X plane side direction, and Cr3: luminance value range of the designated area in the projection drawing in the Y-Z plane side direction. If it is not necessary to make a distinction among those three value ranges, it is denoted as the luminance value range Cr) (S143).

For example, the luminance value range calculation section 33 detects from the pixel group of the cluster C3, which is assumed as the bone area, a minimum pixel value Pmin and a maximum pixel value Pmax, and obtains the range from Pmin to Pmax as the luminance value range Cr of the cluster C3.

Referring to FIG. 7 again, the area judgment section 32 scans the voxels on the virtual ray R in the projecting direction, with respect to each pixel within the designated area, and identifies the voxels having the voxel value V included in the luminance value range Cr, as the bone candidate area (S15).

Firstly, an explanation will made as to the case where the area judgment section 32 detects the bone candidate area based on the luminance value range Cr1 in the designated area of the projection drawing in the X-Y plane side direction. For example, the area judgment section 32 extracts a record in which a designated area flag is set in the designated area flag storage field 23d of the pixel data table 230, and the projecting direction information storage field 23a stores information that specifies the projecting direction as the X-Y plane side direction. Then, the area judgment section 32 acquires the pixel position from the pixel position storage field 23b of the record being extracted.

Then, the area judgment section 32 detects coordinate positions of all the voxels located on the virtual ray R, based on the pixel position and the projecting direction information (here, the X-Y plane side direction). By way of example, if the pixels position is (A, B), the voxels whose coordinate positions are (A, B, (1 to Zn)) are targeted for the scanning ("Zn" indicates the number of voxels in the Z direction).

Subsequently, the area judgment section 32 extracts a record whose voxel position agrees with any of the coordinate positions (A, B, (1 to Zn)) of the voxels located on the virtual ray R, in the voxel position storage field 22a of the voxel data table 220. The area judgment section 32 further extracts a record, whose voxel value V stored in the voxel value storage field 22b of the record being extracted falls into the luminance value range Cr1.

Subsequently, the area judgment section 32 sets a direction flag in the X-Y plane side direction flag storage field 22d of the record being extracted. The processing above is executed as to all the pixels within the designated area. Furthermore, the area judgment section 32 executes the similar processing by using the luminance value range Cr2 for the pixels within the designated area of the projection drawing in the Z-X plane side direction, and by using the luminance value range Cr3 for the pixels within the designated area of the projection drawing in the Y-Z plane side direction.

Figure 9:
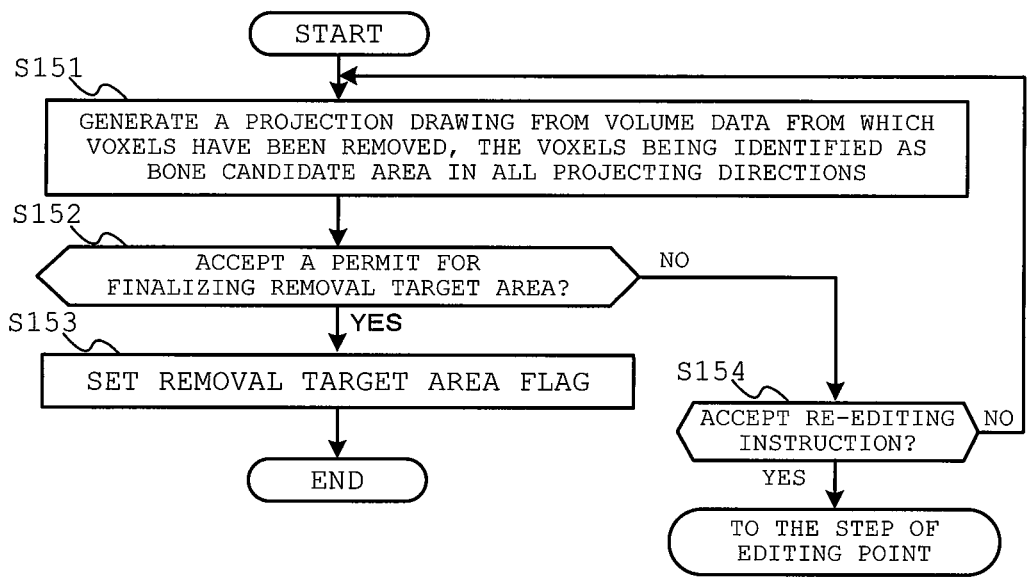
FIG. 9 is a flowchart showing a flow of a process for identifying a removal target area in the image processing apparatus relating to the first embodiment.

Next, the area judgment section 32 specifies as a removal target area, the voxels identified as the bone candidate area in all the projecting directions (S16). Hereinafter, with reference to the flowchart as shown in FIG. 9, a process for specifying the removal target area will be explained.

The image processing section 31 specifies a record from the voxel data table 220, except the record in which the direction flag is set in all the following fields; the X-Y plane side direction flag storage field 22d, the Z-X plane side direction flag storage field 22e, and the Y-Z plane side direction flag storage field 22f. Then, the image processing section 31 projects the volume data made up of only the voxel data stored in this specified record from any projecting direction, generates a projection drawing, and then displays the projection drawing on the display unit 5 (see S151 and FIG. 5(d)).

Next, the area judgment section 32 accepts a permit to finalize the removal target area, via the input part 40 from the user (S152).

If the bone area is removed and a desired result is obtained in the projection drawing displayed on the display unit 5, for instance, the user is allowed to execute an instructing operation to permit finalization of the removal target area via the input part 40. On the other hand, if a desired result is not obtained, such as the bone area has not been removed sufficiently, the user is allowed to input an instructing operation for re-editing via the input part 40 (S154).

In the step 152, upon accepting the permit to finalize the removal target area (YES), the area judgment section 32 extracts a record from the voxel data table 220, the record in which the direction flag is set in all the following fields; the X-Y plane side direction flag storage field 22d, the Z-X plane side direction flag storage field 22e, and the Y-Z plane side direction flag storage field 22f. Then, the area judgment section sets a removal target area flag in the removal target area flag storage field 22c of the record being extracted, specifies the voxels corresponding to the removal target area, and terminates the process (S153).

In the step 154, upon accepting the instructing operation of re-editing (YES), the area judgment section 32 jumps to the step of the point for re-editing. There are provided multiple points for the re-editing point, such as the point of specifying the designated area (S13) and the point of identifying the cluster of the bone area (S142), and the user is allowed to select any of the defined re-editing points.

The image processing section 31 removes the voxels identified as the removal target area, as to the volume data on which the removal target area is specified according to the procedure as described above, and reconstructs the volume data.

It is to be noted that the processing for removing the removal target area can be implemented according to the following procedure, for instance; a mean value of the pixel values of the cluster is calculated, the cluster being assumed as the background area in the clustering process (see FIG. 6, C1), and the voxel value V of the voxels on which the removal target area flag is set is overwritten by the mean value. As a matter of course, the procedure is not limited to the method as described above, and it is alternatively possible to execute a process such as subtracting the voxel value V of the voxels on which the removal target area flag is set, and thereafter the voxels are combined.

In the process for creating the histogram, the pixel segment serving as the unit of the frequency distribution may be a predefined value, or it may be configured as settable by the user.

Furthermore, when the projection drawing from which the bone area is removed is displayed (see FIG. 5(d)), the image processing section 31 is able to use a predetermined value as the voxel value V of the voxels in the removal target area. In the configuration as described above, according to the change of the color or the like of the removal target area, the user is allowed to confirm intuitively whether or not the removal process has been executed.

It is to be noted that the removal target area is not limited to the bone area. It is further possible to configure such that voxels provided with a large luminance value such as a noise can be determined as a removal target.

With the configuration as described above, the image processing apparatus 10 relating to the present embodiment is able to identify the bone area as the removal target according to the clustering process, out of multiple designated areas having been roughly specified in such a manner that the bone area forms a maximum area, and the user is allowed to remove a desired area spatially according to a simple operation.

Figure 10:
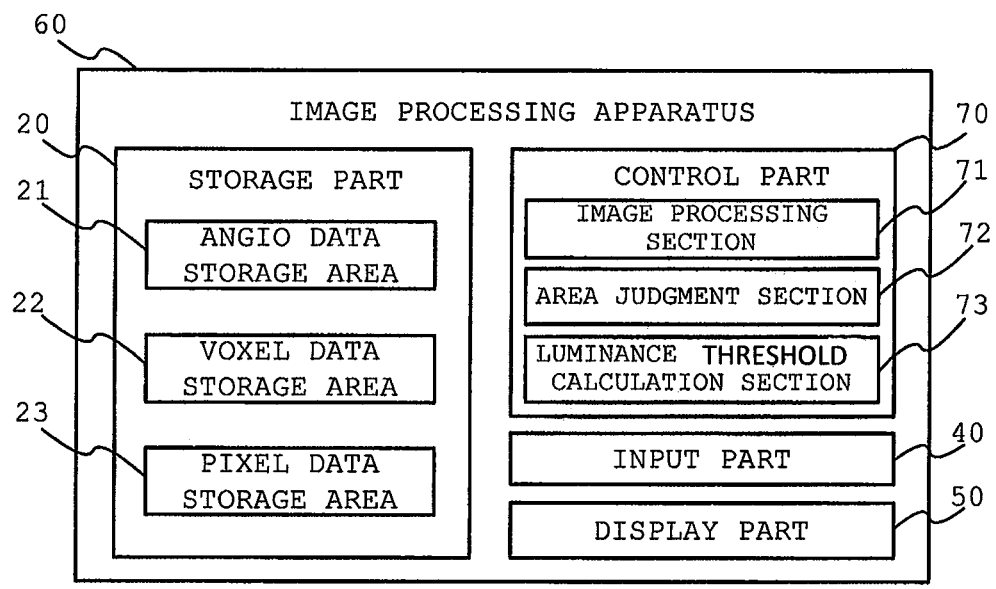
FIG. 10 is a block diagram showing a functional configuration of the image processing apparatus relating to a second embodiment of the present invention.

Next, an image processing apparatus 60 relating to a second embodiment of the present invention will be explained. As shown in FIG. 10, the image processing apparatus 60 incorporates the storage part 20, a control part 70, the input part 40, and the display part 50.

In the image processing apparatus 60 according to the second embodiment, the process executed by the control part 70 is different from the image processing apparatus 10 according to the first embodiment. Therefore, hereinafter, an explanation will be made regarding such differences.

Figure 5:
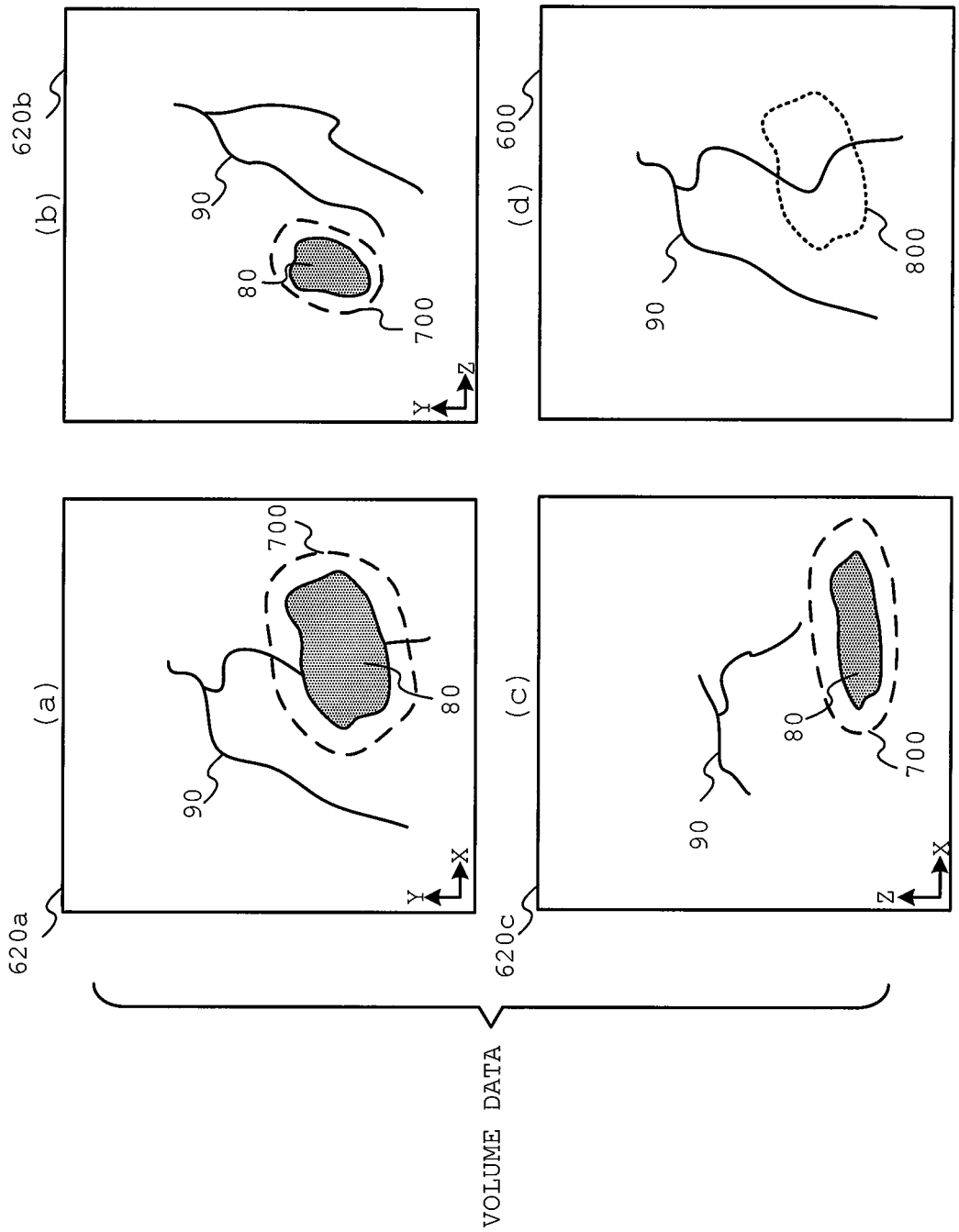
FIG. 5(a) is a schematic diagram showing a projection drawing viewed from the direction of the X-Y plane (front) side of the volume data.
FIG. 5(b) is a schematic diagram showing a projection drawing viewed from the direction of the Y-Z plane (lateral) side of the volume data.
FIG. 5(c) is a schematic diagram showing a projection drawing viewed from the direction of the Z-X plane (top) side of the volume data.
FIG. 5(d) is a schematic diagram showing a projection drawing 600 viewed from the direction of the X-Y plane (front) side of the volume data 610 where the removal target area has been removed.

The control part 70 incorporates an image processing section 71, an area judgment section 72, and a luminance threshold calculation section 73. With reference to FIG. 4 and FIG. 5, processing of these elements will be specifically explained.

The image processing section 71 executes a processing for generating a projection drawing from the volume data according to the MIP method. In addition, the image processing section reconstructs the volume data from the information stored in the voxel data table 220.

The area judgment section 72 accepts from a user via the input part 40, an operation for specifying a rough bone area 80 in such a manner that the bone area forms a maximum area in the projection drawing 620, detects a designated area 700 as to each projection drawing, and identifies a pixel position included in the designated area 700. Furthermore, the area judgment section 72 determines as the bone candidate area, the voxel having the voxel value V, which is equal to or higher than the after-mentioned luminance threshold ThP and also equal to or higher than ThV, on the virtual ray R which projects each of the pixel within the designated area. In addition, the area judgment section identifies the voxel determined as corresponding to the bone candidate area, with regard to all the projecting directions, as the removal target area 800 which is a target for removal.

The luminance threshold calculation section 73 detects a maximum pixel value Pmax, out of the pixel values P of the pixels included in each designated area 700. Subsequently, the luminance threshold calculation section 73 scans the voxels on the virtual ray R projecting the pixels included in the designated area 700, and detects the maximum voxel value Vmax. The luminance threshold calculation section 73 multiplies the pixel value Pmax by a parameter A, and multiples the voxel value Vmax by a parameter B, thereby calculating the luminance thresholds ThP and ThV.

The luminance thresholds ThP and ThV are values which are provided for specifying the range of the voxel value V assumed as the bone area. In the present embodiment, the voxel having the voxel value V satisfying the conditions; ThP$\leqq$V and ThV$\leqq$V, is determined as the bone candidate area.

Here, for the Pmax and Vmax, if any pixel representing a blood vessel is included in the designated area, the pixel value of the pixel representing the blood vessel may be assumed as the maximum value. The parameter A and the parameter B are provided in order to avoid that the voxel having the luminance value representing the blood vessel is recognized as the bone area. Therefore, the parameter A and the parameter B are values less than one, and in the present embodiment, it is preferable that the value is around 0.8, for instance. It is to be noted that the parameter A and the parameter B may be freely configured by the user, considering the luminance value and the like of the angio data.

Figure 11:
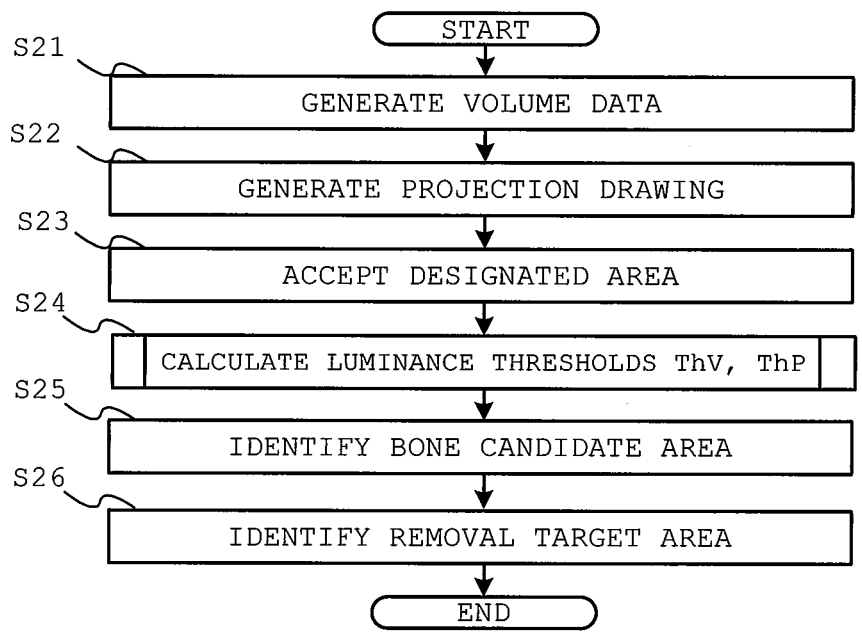
FIG. 11 is a flowchart showing a flow of the process in the image processing apparatus relating to the second embodiment.
Figure 12:
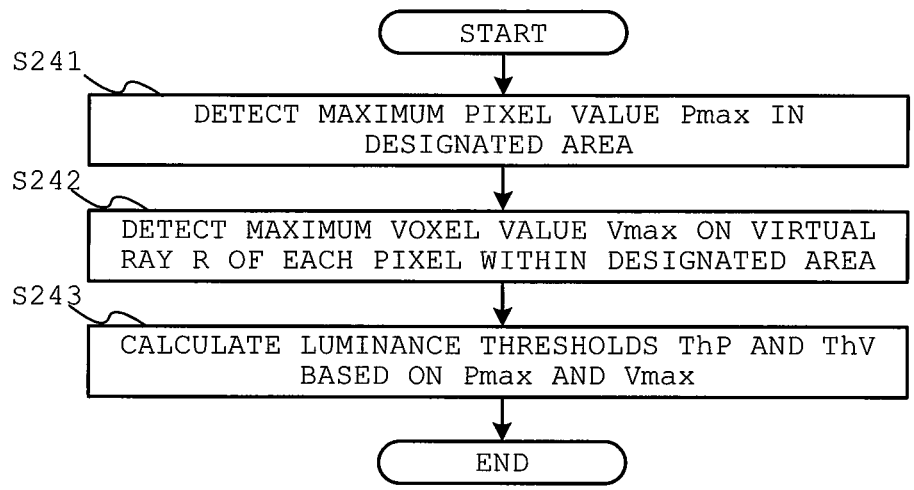
FIG. 12 is a flowchart showing a flow of a process for calculating a luminance threshold in the image processing apparatus relating to the second embodiment.

With reference to the flowcharts as shown in FIG. 11 and FIG. 12, an explanation will be made as to the processing of the image processing apparatus 60 according to the present embodiment configured as described above.

Since the processes from the step 21 to step 23 as shown in FIG. 11 are the same as those from the step 11 to step 13 which are executed in the image processing apparatus 10 relating to the first embodiment, detailed explanation will not be tediously made.

Hereinafter, with reference to FIG. 12, a detailed explanation will be made as to the processing in the step 24. FIG. 12 is a flowchart showing the luminance threshold calculation process that is executed by the image processing apparatus 60 relating to the second embodiment.

The luminance threshold calculation section 73 detects maximum pixel values Pmax1, Pmax2, and Pmax3 out of the pixel values P of the pixels, respectively included in the designated areas of the projection drawings (here, Pmax1: the maximum pixel value of the designated area in the projection drawing in the X-Y plane side direction, Pmax2: the maximum pixel value of the designated area in the projection drawing in the Z-X plane side direction, and Pmax3: the maximum pixel value of the designated area in the projection drawing in the Y-Z plane side direction. If it is not necessary to make a distinction among these three values, the maximum pixel value is denoted as Pmax. (S241). Hereinafter, an explanation will be made as to the case where the luminance threshold calculation section 73 calculates the luminance threshold value from the designated area of the projection drawing in the X-Y plane side direction.

The luminance threshold calculation section 73 extracts a record in which a designated area flag is set in the designated area flag storage field 23*d* of the pixel data table 230, and stores information specifying the X-Y plane side direction in the projecting direction information storage field 23*a*. Next, a maximum pixel value Pmax1 is detected from the pixel value storage field 23*c* of the record being extracted.

The luminance threshold calculation section 73 further scans the voxels on the virtual ray R in the projecting direction as to all the pixels included in the designated area in each projection drawing, and detects a maximum voxel value (X, Y, Z) (S242). By way of example, the luminance threshold calculation section 73 extracts a record in which a designated area flag is set in the designated area flag storage field 23*d* of the pixel data table 230, and stores information specifying the X-Y plane side direction in the projecting direction information storage field 23*a*. Then, the luminance threshold calculation section acquires a pixel position from the pixel position storage field 23*b* of the record being extracted.

Next, the luminance threshold calculation section 73 detects coordinate positions of all the voxels located on the virtual ray R, based on the pixel position and the projecting direction information (in this example here, it is the X-Y plane side direction). By way of example, if the pixel position is (A, B) and the projecting direction information specifies the X-Y plane side direction, the voxels whose coordinate positions are (A, B, (1 to Zn)) are targeted for the scanning (here, "Zn" represents the number of voxels in the Z-direction).

Subsequently, the luminance threshold calculation section 73 refers to the voxel position storage field 22*a* of the voxel data table 220, and extracts a record storing the voxel position that agrees with any of the coordinate positions (A, B, (1 to Zn)) of the voxels located on the virtual ray R. The luminance threshold calculation section 73 detects a maximum voxel value Vmax from the voxel value storage field 22*b* of the record being extracted.

Furthermore, the luminance threshold calculation section 73 calculates a luminance threshold ThP1 based on the pixel value Pmax1, and the luminance threshold ThV based on the voxel value Vmax (S243). By way of example, the luminance threshold calculation section 73 multiplies the pixel value Pmax1 by the parameter A, and multiples by the parameter B, each voxel value Vmax which is detected on the virtual ray R projecting each of the pixels within the designated area, thereby obtaining the luminance threshold ThP1, and ThV for each pixel.

This processing is executed for each of the designated areas, and the luminance thresholds for the Z-X plane side direction and the luminance thresholds for the Y-Z plane side directions are calculated as well.

Referring to FIG. 11 again, the area judgment section 72 scans the voxels on the virtual ray R which projects each of the pixels within the designated area of each projection drawing, and specifies as the bone candidate area, the voxels having the voxel value V equal to or higher than the luminance threshold ThP, and equal to or higher than ThV which is calculated from Vmax detected from the virtual ray R projecting the pixel (S25). Hereinafter, an explanation will be made as to the case where the area judgment section 72 specifies the bone candidate area from the designated area of the projection drawing in the X-Y plane side direction.

The area judgment section 72 extracts a record in which a designated area flag is set in the designated area flag storage field 23*d* of the pixel data table 230, and which stores information specifying the X-Y plane side direction in the projecting direction information storage field 23*a*. Then, the area judgment section 72 acquires a pixel position from the pixel position storage field 23b of the record being extracted.

Thereafter, the area judgment section 72 detects the coordinate positions of all the voxels located on the virtual ray R, from the pixel position and the projecting direction information (here, the X-Y plane side direction). Subsequently, the area judgment section 72 extracts a record whose voxel position corresponds to the voxel coordinate position located on the virtual ray R, from the voxel data table 220 in the voxel position storage field 22a. The area judgment section 72 extracts a record having the voxel value V equal to or higher than the luminance threshold ThP1, and equal to or higher than ThV calculated from the Vmax that is detected from the virtual ray R projecting the pixel, and sets the direction flag in the X-Y plane side direction flag storage field 22d of the record being extracted. Furthermore, the area judgment section 72 scans voxels having the voxel value V equal to or higher than a luminance threshold ThP2 and equal to or higher than ThV detected from the virtual ray R projecting the pixel which is included in the designated area of the projection drawing in the Z-X plane side direction, and sets the direction flag thereof; and scans voxels having the voxel value V equal to or higher than a luminance threshold ThP3 and equal to or higher than ThV detected from the virtual ray R projecting the pixel which is included in the pixels within the designated area of the projection drawing in the Y-Z plane side direction, and sets the direction flag thereof.

Since the process in the step 26 is the same as that of the step 16 which is executed in the image processing apparatus 10 relating to the first embodiment, detailed explanation will not be made tediously.

In addition, as to the volume data in which the removal target area has been identified, the image processing section 71 removes the voxels specified as the removal target area, and reconstructs the volume data.

It is to be noted that at the re-editing point that is used in the process of step 26, it is possible to provide a point for specifying the designated area (S23) and a point for changing the parameters A and B used in the step 243.

With the configuration above, the image processing apparatus 60 according to the present embodiment is able to identify the bone area which is spatially targeted for removal, out of the roughly designated areas in multiple projection drawings, by using the luminance value of the bone area and parameters. Therefore, the user is allowed to remove a desired area according to a simple operation.

What is claimed is:

1. An image processing apparatus for projecting a three-dimensional image from any projecting direction and generating multiple projection drawings, comprising,
    an input accepting section for displaying the multiple projection drawings on a display part, and accepting an input of a designated area including a removal target area as to each of the projection drawings,
    a luminance value calculation section for specifying a luminance value of the removal target area from the designated area, and
    an area judgment section for determining as the removal target area, an area having the luminance value within a specific range, out of the image located on a virtual ray which projects the designated area, as to each of the multiple projection drawings,
    wherein the luminance value calculation section:
    detects a maximum luminance value for each designated area, out of the luminance values of the pixels constituting the designated area,
    detects a maximum luminance value, for each virtual ray projecting each pixel, out of the luminance values of the voxels constituting the three-dimensional image and located on the virtual ray projecting each of the pixels constituting the designated area, and
    calculates a first luminance threshold and a second luminance threshold, respectively by multiplying the maximum luminance value out of the luminance values of the pixels, by a first predetermined parameter, and multiplying the maximum luminance value out of the luminance values of the voxels, by a second predetermined parameter, and
    wherein the area judgment section:
    detects a voxel having the luminance value equal to or higher than the first luminance threshold associated with the designated area, and equal to or higher than the second luminance threshold associated with the pixel within the designated area, out of the voxels located on the virtual ray projecting each of the pixels within the designated area, and
    determines as the removal target area, a voxel judged as satisfying a condition having the luminance value equal to or high than the first luminance threshold and equal to or high than the second luminance threshold, in all the projecting directions.

2. The image processing apparatus according to claim 1, wherein,
    the luminance value calculation section detects a distribution for each luminance value range regarding pixels constituting the designated area, as to each designated area, and acquires the luminance value range where the distribution of pixels indicates a maximum frequency, and
    the area judgment section detects a voxel having a luminance value within the luminance value range associated with the designated area, out of the voxels constituting the three-dimensional image and located on the virtual ray that projects each of the pixels within the designated area, and determines as the removal target area, the voxel having the luminance value within the luminance value range associated with the designated area, in all the projecting directions.

3. The image processing apparatus according to claim 1, wherein,
    the three-dimensional image is made up of multiple tomographic images of a living body, and
    the removal target area is a bone area having a luminance value higher than the luminance value of blood vessel.

4. The image processing apparatus according to claim 1, wherein,
    via the input accepting section, the area judgment section accepts a selecting operation in such a manner that the removal target area forms a maximum area within the designated area.

5. The image processing apparatus according to claim 1, further comprising,
    an image processing section for generating the projection drawing and the three-dimensional image, after removing the voxel determined as the removal target area.

6. A method for allowing a computer to function as an image processing apparatus for projecting a three-dimensional image from any projecting direction and generating multiple projection drawings, the computer having:
    an input accepting section for displaying the multiple projection drawings on a display part, and accepting an input of a designated area including a removal target area as to each of the projection drawings, a luminance value calculation section for specifying a luminance value of the removal target area from the designated area, and an area judgment section for determining as the removal target area, an area having the luminance value within a specific range, out of the image located on a virtual ray which projects the designated area, as to each of the multiple projection drawings, wherein the luminance value calculation section performs the steps of:

detecting a maximum luminance value for each designated area, out of the luminance values of the pixels constituting the designated area, detecting a maximum luminance value, for each virtual ray projecting each pixel, out of the luminance values of the voxels constituting the three-dimensional image and located on the virtual ray projecting each of the pixels constituting the designated area, and calculating a first luminance threshold and a second luminance threshold, respectively by multiplying the maximum luminance value out of the luminance values of the pixels, by a first predetermined parameter, and multiplying the maximum luminance value out of the luminance values of the voxels, by a second predetermined parameter, and wherein the area judgment section performs the steps of:

detecting a voxel having the luminance value equal to or high than the first luminance threshold associated with the designated area, and equal to or higher than the second luminance threshold associated with the pixel within the designated area, out of the voxels located on the virtual ray projecting each of the pixels within the designated area, and determining as the removal target area, a voxel judged as satisfying a condition having the luminance value equal to or higher than the first luminance threshold and equal to or higher than the second luminance threshold, in all the projecting directions.

7. The program according to claim 6, wherein, the luminance value calculation section detects a distribution for each luminance value range regarding pixels constituting the designated area, as to each designated area, and acquires the luminance value range where the distribution of pixels indicates a maximum frequency, the area judgment section detects a voxel having a luminance value within the luminance value range associated with the designated area, out of the voxels constituting the three-dimensional image and located on the virtual ray that projects each of the pixels within the designated area, and determines as the removal target area, the voxel having the luminance value within the luminance value range associated with the designated area, in all the projecting directions.

* * * * *